(12) United States Patent
Ashwood et al.

(10) Patent No.: US 6,515,126 B2
(45) Date of Patent: Feb. 4, 2003

(54) CHEMICAL SYNTHESIS OF SPIROCYCLIC PIPERIDINES BY DOUBLE RING-CLOSING METATHESIS

(75) Inventors: Michael Stewart Ashwood, Bishops Stortford (GB); Ian Frank Cottrell, Hertford (GB); Cameron John Cowden, Stanstead Abbotts (GB); Debra Jane Wallace, Stanstead Abbotts (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/794,940

(22) Filed: Feb. 27, 2001

(65) Prior Publication Data

US 2001/0029297 A1 Oct. 11, 2001

(30) Foreign Application Priority Data

Feb. 28, 2000 (GB) .............................. 0004699

(51) Int. Cl.$^7$ ........................................... C07D 221/20
(52) U.S. Cl. ........................................................ 546/16
(58) Field of Search ........................................... 546/16

(56) References Cited

FOREIGN PATENT DOCUMENTS

| WO | WO97/49710 | 12/1997 |
| WO | WO98/13369 | 4/1998 |
| WO | WO98/49170 | 11/1998 |
| WO | WO98/54187 | 12/1998 |

OTHER PUBLICATIONS

Guillermo C. Bazan, et al., *J. Am. Chem. Soc.*, 1991, 113, 6899–6907.
Robert H. Grubbs, et al., *Tetrahedron*, 54 (1998) 4413–4450.
SonBinh T. Nguyen, et al., *J. Am. Chem. Soc.*, 1992, 114, 3974–3975.
SonBinh T. Nguyen, et al., *Journal of Organometallic Chemistry*, 497 (1995) 195–200.
Peter Schwab, et al., Angew, *Chem. Int. Ed. Engl.*, 1995, 34, No. 18, 2039–2041.
Peter Schwab, et al., *J. Am. Chem. Soc.*, 1996, 118, 100–110.

Primary Examiner—Patricia L. Morris
(74) Attorney, Agent, or Firm—J. Eric Thies; Melvin Winokur

(57) ABSTRACT

The present invention relates to a process for the preparation of a compound of formula (I)

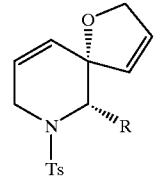

(I)

wherein Ts is a tosylate group and R is an alkyl group, an unsubstituted phenyl or substituted phenyl ring, or a benzyl or substituted benzyl group; which comprises:

(i) cyclising a compound of formula (II)

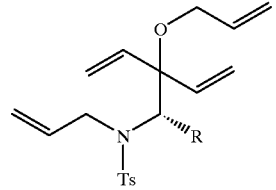

(II)

in the presence of a suitable catalyst; and (ii) purifying and collecting the resultant compound of formula (I).

3 Claims, No Drawings

CHEMICAL SYNTHESIS OF SPIROCYCLIC PIPERIDINES BY DOUBLE RING-CLOSING METATHESIS

The present invention relates to spirocyclic piperidine compounds and to the preparation thereof. The spirocyclic piperidine compounds of the present invention are useful as intermediates in the synthesis of therapeutic agents. In particular the spirocyclic piperidine compounds of the present invention are useful as intermediates in the synthesis of certain neurokinin-1 (NK-1) receptor antagonists.

Compounds of formula (A) below, which are described in a number of published patent specifications (WO 97/49710, WO 98/13369, WO 98/49170 and WO 98/54187), are potent and selective NK-1 receptor antagonists.

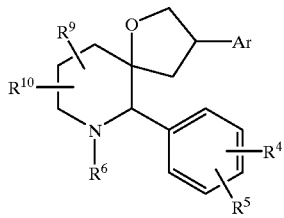

(A)

wherein
Ar represents a group selected from:

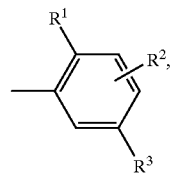

(a)

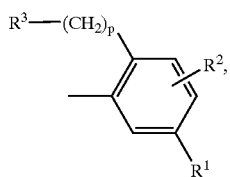

(b)

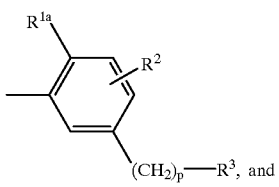

(c)

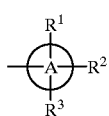

(d)

$R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^aR^b$, $SR^a$, $SOR^a$, $SO_2R^a$ or $OSO_2R^a$, where $R^a$ and $R^b$ each independently represent hydrogen, $C_{1-4}$alkyl or fluoro$C_{1-4}$alkyl;

$R^{1a}$ represents halogen, hydroxy, $C_{1-6}$alkyl, $C_{1-6}$alkoxy, $C_{1-6}$alkylthio, $C_{1-6}$alkoxy$C_{1-4}$alkyl, fluoro$C_{1-6}$alkyl, fluoro$C_{1-6}$alkoxy, fluoro$C_{1-6}$alkylthio, fluoro$C_{1-6}$alkoxy$C_{1-4}$alkyl, $C_{3-7}$cycloalkyl, $C_{3-7}$cycloalkyl$C_{1-4}$alkyl, $C_{2-6}$alkenyloxy, cyano, phenoxy, benzyloxy, $NR^aR^b$, $SR^a$, $SOR^a$, $SO_2R^a$, or $OSO_2R^a$, where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$ or $R^{1a}$, they may be joined together such that there is formed a 5- or 6-membered saturated or unsaturated ring containing one or two oxygen atoms;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{14}$, $NR^aSO_2R^{14}$, or $C_{1-4}$alkyl substituted by cyano or $CO_2R^a$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, $CN$, $SR^a$, $SOR^a$, $SO_2R^a$, $COR^a$, $CO_2R^a$, phenyl, $—(CH_2)_rNR^aR^b$, $—(CH_2)_rNR^aCOR^b$, $—(CH_2)_rCONR^aR^b$, or $CH_2C(O)R^a$, where $R^a$ and $R^b$ are each independently hydrogen or $C_{1-4}$alkyl and r is zero, 1 or 2;

$R^4$ represents hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}$alkyl$R^{12}$, $CONR^{13}C_{2-6}$alkenyl, $CONR^{13}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula $—CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by $=O$ or $=S$ and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group $S(O)$ or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^e$, oxo, $CO_2R^a$ or $CONR^aR^b$ where $R^a$ and $R^b$ are as previously defined and $R^e$ represents hydrogen, $C_{1-6}$alkyl or phenyl;

$R^{12}$ represents $OR^a$, $CONR^aR^b$ or heteroaryl;

$R^{13}$ represents hydrogen or $C_{1-6}$alkyl;

$R^{14}$ represents $C_{1-6}$alkyl, $C_{1-6}$alkoxy, fluoro$C_{1-6}$alkyl or phenyl; and p is zero or 1;

and pharmaceutically acceptable salts thereof.

The aforementioned patent specifications describe the synthesis of compounds of formula (A) by a variety of methods. In particular, two useful intermediates are compounds of formula (B) and (C)

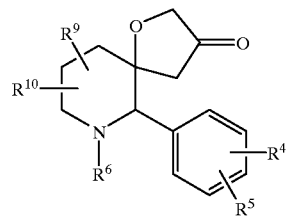
(B)

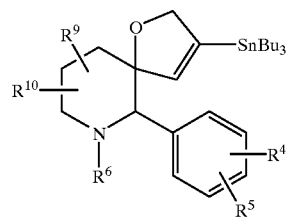
(C)

Synthetic routes for the preparation of these compounds are described in the following reaction schemes:

Scheme A

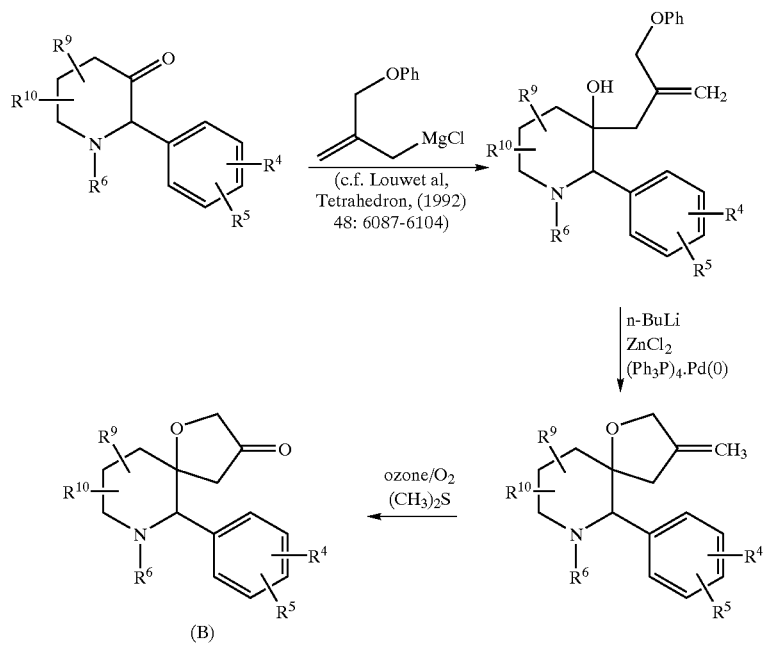

Scheme B

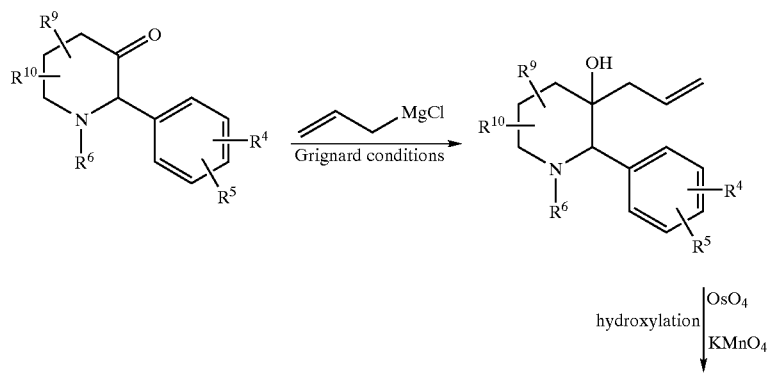

-continued
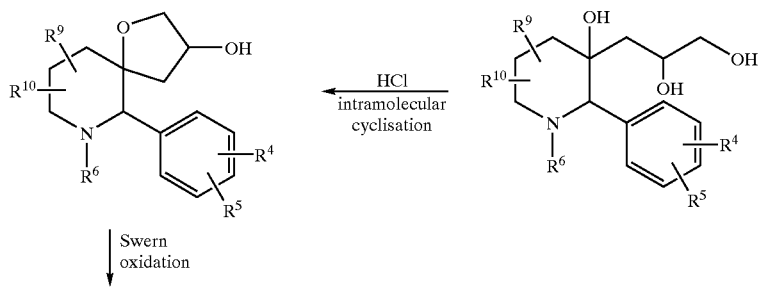
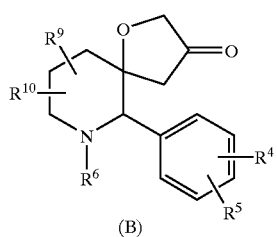
(B)
Scheme C
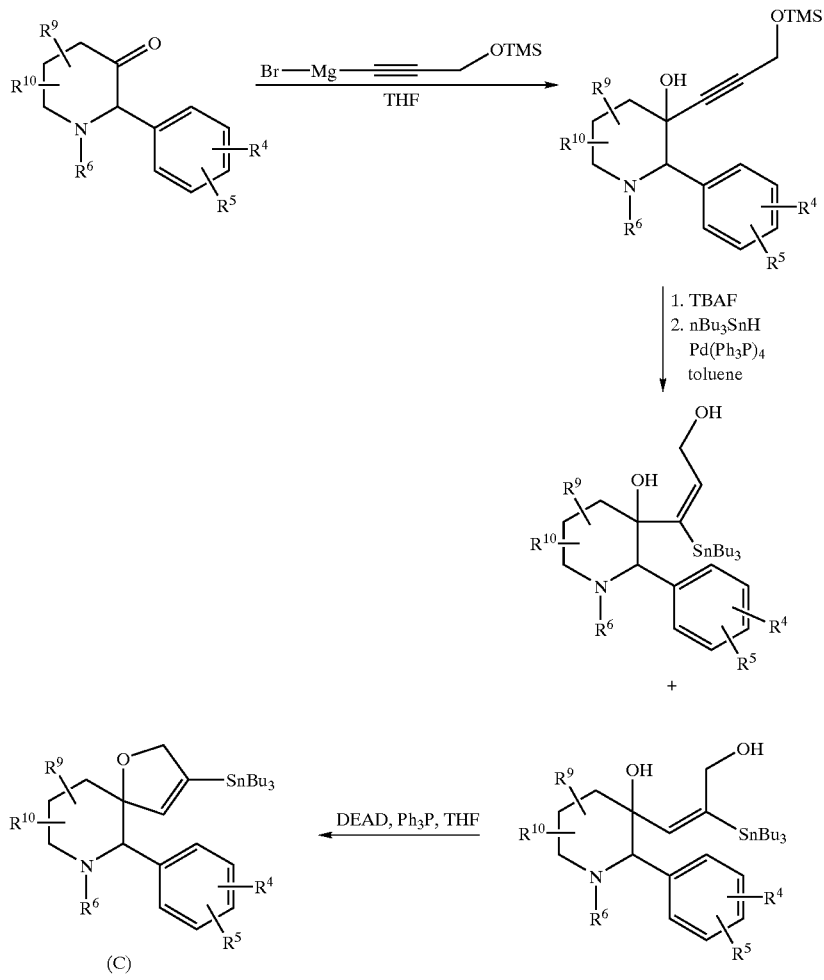
(C)

Another useful intermediate in the synthesis of compounds of formula (A) are compounds of formula (D).

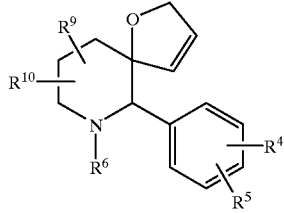
(D)

Compounds of formula (D) may be prepared, for example, by conversion of a stannane of formula (C) to the corresponding iodide by treatment with iodine at reduced temperature, for example, at about −78° C., in a suitable solvent such as dichloromethane. The iodine may then be displaced to give the compound of formula (D) by treatment with, for example, α,α'-azo-isobutyronitrile and tributyltin hydride in a suitable solvent, for example, toluene, at an elevated temperature, for example, at about 100° C.

Alternatively, compounds of formula (D) may be prepared by the cyclisation of a compound of formula (E)

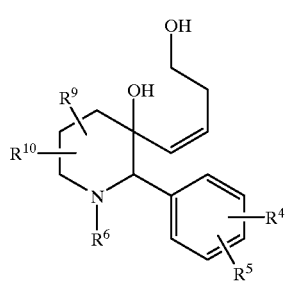
(E)

using suitable dehydrating reagents, for example, methanesulfonyl chloride or benzenesulfonyl chloride in pyridine or triethylamine in an organic solvent such as dichloromethane, or using triphenylphosphine and diethylazodicarboxylate in a suitable solvent such as tetrahydrofuran.

The preferred compounds of formula (A) are reported to have a 5R, 6S stereochemistry, for example, as shown in formula (F)

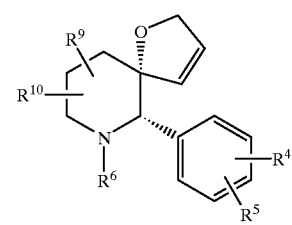
(F)

Thus, for instance, International Patent Specification No. WO 97/49710 (cross-referring also to European Patent Publication No. 0 528 495-A) describes the synthesis of (5R, 6S)-6-phenyl-1-oxa-7-(tert-butoxycarbonyl)aza-spiro[4,5]dec-3-ene in an eight step synthesis from methyl 4-nitrobutyrate and benzaldehyde (Scheme D):

Scheme D

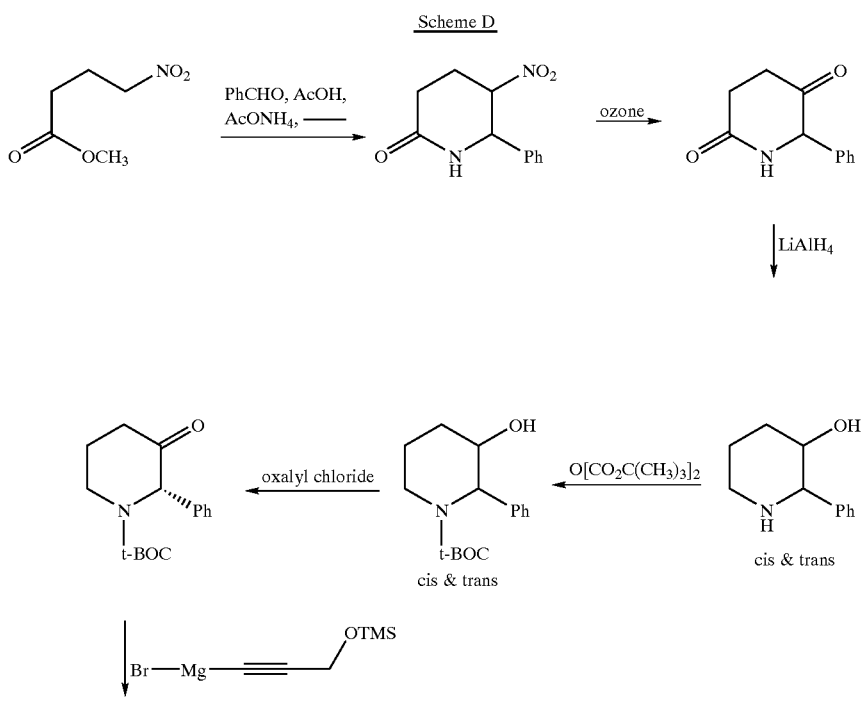

-continued

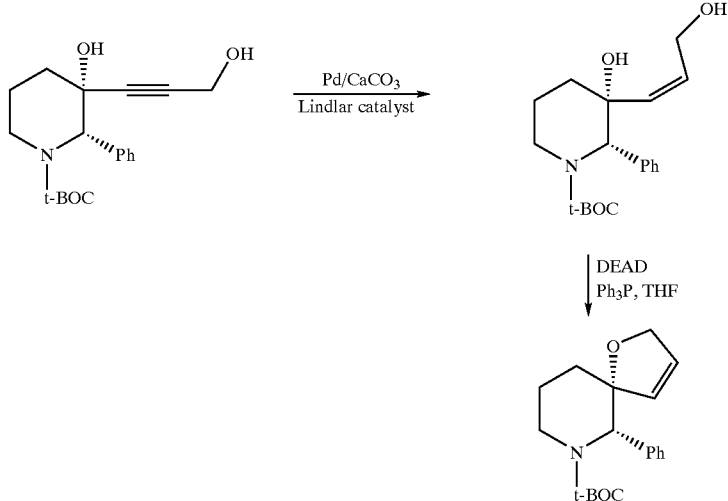

We have now found a high yielding process for the rapid, stereocontrolled synthesis of functionalised spirocyclic piperidine compounds useful as intermediates in the synthesis of compounds such as those described in the aforementioned International Patent Specifications. The process utilises a multiple ring-closing metathesis (RCM) reaction to form the spirocycle, with relative stereochemistry being directed by the choice of substituent on the nitrogen atom. The reaction occurs under mild conditions and is tolerant of a wide range of functional groups. The products are amenable to further selective transformations.

A particular advantage of the process of the present invention is the fact that the process comprises significantly fewer reaction steps, compared with the conventional eight step reaction sequence. This short synthetic sequence is therefore more efficient for large scale synthesis, and affords less opportunity for unwanted side-reactions.

Another advantage of the process of the present invention is that both stereoisomers are accessible in a stereocontrolled manner. According to the conventional methodology, optically pure intermediates were obtained by resolution techniques, resulting in the production of a considerable amount of undesired isomer as a waste by-product.

The product of the multiple ring-closing metathesis reaction is amenable to further reaction in a stereocontrolled and regiocontrolled fashion. In this way pharmacologically interesting compounds such as those described in the aforementioned International Patent Specifications can be synthesised in a highly convergent and efficient way.

Thus, in a first aspect of the present invention, there is provided a process for the preparation of a compound of formula (I)

(I)

wherein Ts is a tosylate group and R is an alkyl group, an unsubstituted phenyl or substituted phenyl ring, or a benzyl or substituted benzyl group; which comprises:

(i) cyclising a compound of formula (II)

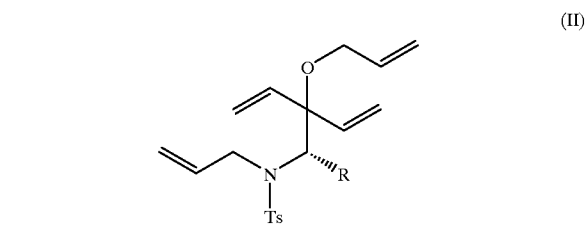

in the presence of a suitable catalyst; and (ii) purifying and collecting the resultant compound of formula (I).

In the compounds of formulae (I) and (II), R is preferably straight or branched $C_{1-4}$alkyl, benzyl, phenyl or substituted phenyl. Where R is substituted phenyl, the phenyl ring is preferably substituted with 1 or 2 substituents as defined for $R^4$ and $R^5$ above.

Most preferably, R represents unsubstituted phenyl or 4-fluorophenyl.

Where R represents a substituted benzyl group, suitable substituents on the phenyl ring of the benzyl group include those defined for $R^4$ and $R^5$ above.

Suitable catalysts of use in step (i) of the present invention include any catalyst or multicomponent catalyst system that initiates olefin metathesis. Preferred catalysts are single component metal carbene complexes. Particularly preferred catalysts include:

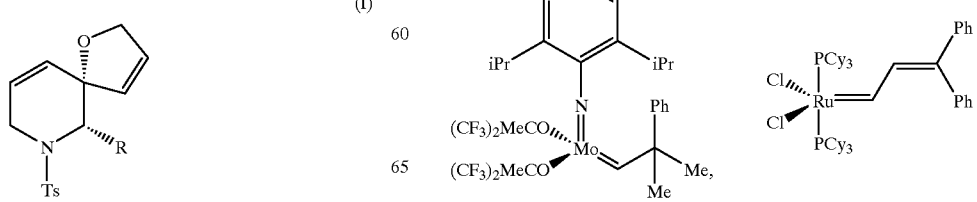

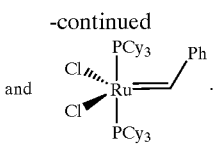 and 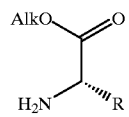

An especially preferred catalyst of use in the present invention is RuCl$_2$(PCy$_3$)$_2$=CHPh, also referred to as Grubbs catalyst. These catalysts and their use is described, for instance, in the following literature:

Bazan et al., *J. Am. Chem. Soc.*, 1991, 113, 6899 and references cited therein.

Nguyen et al., *J. Am. Chem. Soc.*, 1992, 114, 3974.

Nguyan and Grubbs, *J. Organomet. Chem.*, 1995, 497, 195.

Schwab et al., *Angew. Chem. Int. Ed. Eng.*, 1995, 34, 2039.

Schwab et al., *J. Am. Chem. Soc.*, 1996, 118, 100.

Grubbs and Chang, *Tetrahedron*, 1998, 54, 4413.

Suitable organic solvents of use in step (i) of the present invention include halogenated hydrocarbons, such as dichloromethane or chloroform.

Step (i) of the present invention is conveniently effected at room temperature and pressure, for example at about 20° C.

Purification of the compound of formula (I) according to step (ii) of the present invention is required to remove the minor fraction of undesired stereoisomer. Purification is conveniently effected using column chromatography, although other conventional techniques known to one of ordinary skill in the art may be used.

Compounds of formula (II) may be prepared by reaction of a compound of formula (III)

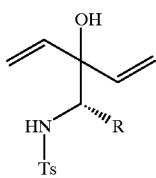

(III)

with an allyl halide, especially allyl bromide, in the presence of sodium hydride in tetrahydrofuran/1,3-dimethyl-3,4,5,6-tetrahydro-2(1H)-pyrimidinone (THF/DMPU). The reaction is conveniently effected at room temperature and pressure, for example, at about 20° C.

Compounds of formula (III) may be prepared by reaction of a compound of formula (IV)

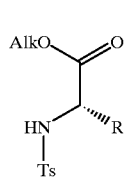

(IV)

wherein Alk is a C$_{1-4}$alkyl residue of the ester moiety, especially methyl, with a Grignard reagent, such as vinylmagnesium bromide, in the presence of cerium chloride. The reaction is conveniently effected in an aprotic solvent such as ether, for example tetrahydrofuran, at a reduced temperature, for example at about 0° C.

Compounds of formula (IV) may be prepared by reaction of an amino acid ester of formula (V)

(V)

or a salt thereof, preferably the hydrochloride salt thereof, with tosyl chloride in the presence of a suitable organic base, for example, triethylamine. The reaction is conveniently effected in an aprotic solvent such as an ether, for example, tetrahydrofuran, at room temperature and pressure, for example at about 20° C.

Compounds of formula (I) are novel compounds and represent a further aspect of the present invention.

It will be appreciated that compounds of formula (A) above, and precursors therefor may be prepared in a conventional manner from the compounds of formula (I). Thus, for example, a reductive Heck reaction using a suitable halogenated aryl or heteroaryl compound (preferably where the halogen is iodine) may be used to introduce the ring Ar, or a precursor therefor. The reductive Heck reaction may be effected using a palladium catalyst such as palladium acetate with, for example, tri-o-tolylphosphine, dimethylformamide and tributylamine, or tetrabutylammonium chloride and dimethylformamide, and a reducing agent, preferably formic acid or a salt thereof, such as potassium formate.

The C$_9$–C$_{10}$ double bond may be removed by conventional hydrogenolysis and likewise the tosylate group removed using techniques well known to the person of ordinary skill in the art.

As stated above, the present invention provides a rapid stereocontrolled synthesis of functionalised spirocyclic piperidine compounds, the relative stereochemistry being directed by the choice of substituent on the nitrogen atom.

Thus, whilst the 5S, 6S compounds of formula (A) are less preferred than their 5R, 6S isomers, such compounds may nevertheless be useful pharmacological agents. The present invention therefore provides an efficient synthetic route to enable the preparation of the 5S, 6S isomers.

Thus, according to another aspect of the present invention, there is provided a process for the preparation of a compound of formula (VI)

(VI)

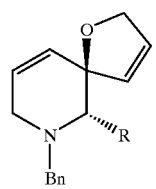

wherein Bn is a benzyl group and R is as previously defined; which comprises:
(i) cyclising a compound of formula (VII)

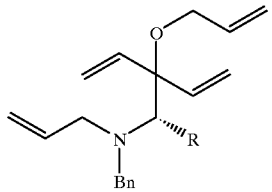

(VII)

in the presence of a suitable catalyst; and
(ii) purifying and collecting the resultant compound of formula (VI).

For the avoidance of doubt, the aforementioned preferences for the group R apply mutatis mutandis to the compounds of formulae (VI) and (VII).

Similarly, the aforementioned catalysts are suitable for use in step (i) of this aspect of the present invention, Grubbs catalyst being preferred.

Suitable organic solvents of use in step (i) of this aspect of the present invention include halogenated hydrocarbons, such as dichloromethane or chloroform. The cyclisation is conveniently effected at room temperature and pressure, for example at about 20° C.

Purification of the compound of formula (VI) according to step (ii) of this aspect of the present invention is required to remove the minor fraction of undesired stereoisomer. Purification is conveniently effected using column chromatography, although other conventional techniques known to one of ordinary skill in the art may be used.

Compounds of formula (VII) may be prepared by reaction of a compound of formula (VIII)

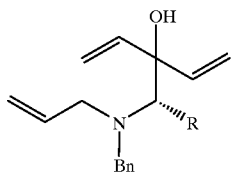

(VIII)

with an allyl halide, especially allyl bromide, in the presence of sodium hydride in tetrahydrofuran/1,3-dimethyl-3,4,5,6-tetrahydro-2(1H)-pyrimidinone (THF/DMPU). The reaction is conveniently effected at room temperature and pressure, for example, at about 20° C.

Compounds of formula (VIII) may be prepared by reaction of a compound of formula (IX)

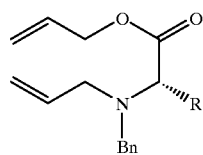

(IX)

with a Grignard reagent, such as vinylmagnesium bromide, in the presence of cerium chloride. The reaction is conveniently effected in an aprotic solvent such as ether, for example tetrahydrofuran, at a reduced temperature, for example at about 0° C.

Compounds of formula (IX) may be prepared by reaction of a compound of formula (X)

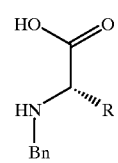

(X)

or a salt thereof, preferably the hydrochloride salt thereof, with an allyl halide, especially allyl bromide, in the presence of a suitable organic base, for example, diisopropylamine. The reaction is conveniently effected in a solvent such as dimethylformamide, at an elevated temperature, for example at about 60° C.

Compounds of formula (X) are readily prepared from the corresponding primary amine by conventional N-benzylation techniques, for example, reaction of the amino acid with benzaldehyde in the presence of a sodium hydroxide, followed by treatment with sodium borohydride.

Compounds of formula (VI) are novel compounds and represent a further aspect of the present invention.

According to a further aspect of the present invention, there is provided a method for the synthesis of the spirocyclic piperidinyl compounds described in International Patent Publication Nos. WO 97/49710, WO 98/13369, WO 98/49170 or WO 98/54187. Alternatively, there is provided a method for the synthesis of compounds of formula (A) as described herein. Said method comprises the double ring closing metathesis reactions described and claimed herein, followed by one or more synthetic steps to complete the synthesis of the desired compound. Suitable methods for completing the synthesis are described in the aforementioned International Patent Publications.

In particular, the use of the double ring closing metathesis reactions described and claimed herein in the preparation of the spirocyclic piperidinyl compounds disclosed in WO 97/49710 is preferred. Especially preferred compounds described in WO 97/49710 include:

(3R,5R,6S)-3-[2-cyclopropoxy-5-(trifluoromethoxy)phenyl]-6-phenyl-1-oxa-7-aza-spiro[4,5]decane;
(3R,5R,6S)-3-[2-cyclopropoxy-5-(difluoromethoxy)phenyl]-6-phenyl-1-oxa-7-aza-spiro[4,5]decane;
(3R, 5R,6S)-3-[2-cyclopropoxy-5-(trifluoromethoxy)phenyl]-6-(4-fluorophenyl)-1-oxa-7-aza-spiro[4,5]decane;
(3R,5R,6S)-3-[2-cyclopropoxy-5-(trifluoromethyl)phenyl]-6-phenyl-1-oxa-7-aza-spiro[4,5]decane;
and pharmaceutically acceptable salts thereof.

Thus, according to a further preferred aspect of the present invention there is provided a process for the preparation of a compound of formula (XVII):

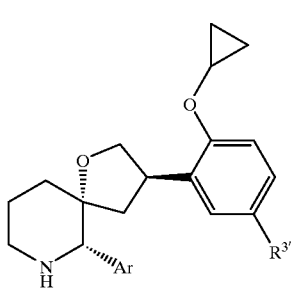

(XVII)

wherein Ar is a phenyl or 4-fluorophenyl group; and

R³' is a trifluoromethyl, trifluoromethoxy or difluoromethoxy group; or a pharmaceutically acceptable salt thereof which comprises:

(i) cyclising a compound of formula (XI)

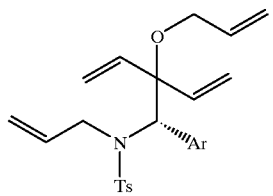
(XI)

in the presence of a suitable catalyst;

(ii) reacting the resultant compound of formula (XII) with a compound of formula (XIII)

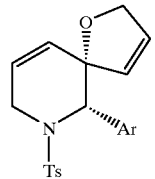
(XII)

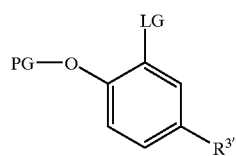
(XIII)

wherein PG is a hydroxy-protecting group, in particular, a benzyl group, and LG is a leaving group such as triflate (—OSO₂CF₃) or a halogen atom, for example, chlorine, bromine or iodine, in particular, iodine, under reductive Heck conditions using a palladium catalyst such as palladium acetate with, for example, tri-o-tolylphosphine, dimethylformamide and tributylamine, or tetrabutylammonium chloride and dimethylformamide or triethylamine, and a reducing agent, preferably lithium chloride and potassium hydrogencarbonate, or formic acid or a salt thereof, such as potassium formate;

(iii) deprotecting and hydrogenating the resultant compound of formula (XIV)

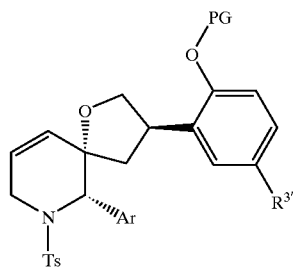
(XIV)

(iv) reacting the resultant phenol of formula (XV)

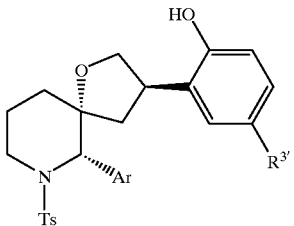
(XV)

with (1-iodo-cycloprop-1-yl)phenylsulfide in the presence of silver carbonate;

(v) reacting the resultant compound of formula (XVI)

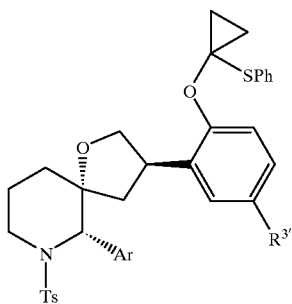
(XVI)

according to either (a) reaction with lithium naphthalenide in a suitable solvent such as an ether, for example, tetrahydrofuran, the reaction being effected at reduced temperature, for example at about −78° C.; or (b) in a first step, oxidation of the phenylthio moiety using, for example, oxone in the presence of aluminium oxide, the reaction being effected in a suitable solvent such as a halogenated hydrocarbon, for example, chloroform, and conveniently at room temperature, and in a second step, removal of the phenylsulfonyl moiety using, for example, sodium amalgam in the presence of disodium hydrogen orthophosphate, the reaction being effected in a suitable solvent such as an alcohol, for example, methanol, and at a reduced temperature, for example, between 0° C. and 10° C.

(vi) purifying and collecting the resultant compound of formula (XVII)

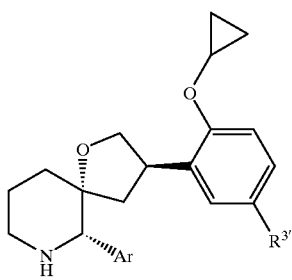
(XVII)

and optionally, said process being followed, where necessary, by the removal of the tosyl protecting group where present;

and/or, if desired, converting the resulting compound or a salt thereof, into a pharmaceutically acceptable salt thereof.

In particular, the compound of formula (XVII) is selected from:

(3R,5R,6S)-3-[2-cyclopropoxy-5-(trifluoromethoxy)phenyl]-6-phenyl-1-oxa-7-aza-spiro[4,5]decane;
(3R,5R,6S)-3-[2-cyclopropoxy-5-(difluoromethoxy)phenyl]-6-phenyl-1-oxa-7-aza-spiro[4,5]decane;
(3R,5R,6S)-3-[2-cyclopropoxy-5-(trifluoromethoxy)phenyl]-6-(4-fluorophenyl)-1-oxa-7-aza-spiro[4,5]decane; and
(3R,5R,6S)-3-[2-cyclopropoxy-5-(trifluoromethyl)phenyl]-6-phenyl-1-oxa-7-aza-spiro[4,5]decane;

or a pharmaceutically acceptable salt thereof.

Suitable catalysts of use in step (i) of this aspect of the present invention are as previously described, Grubbs catalyst being preferred.

Suitable organic solvents of use in step (i) of this aspect of the present invention include halogenated hydrocarbons, such as dichloromethane or chloroform. The cyclisation is conveniently effected at room temperature and pressure, for example at about 20° C.

Suitable hydrogenation conditions of use in step (iii) of this aspect of the present invention include catalytic hydrogenation in the presence of a metal catalyst such as palladium or platinum or hydroxides or oxides thereof, preferably in a suitable solvent such as an alcohol, for example, methanol, an ester, for example, ethyl acetate, or an organic acid, for example, acetic acid, or a mixture thereof.

Step (v) of this aspect of the present invention is preferably effected at a reduced temperature, for example, at about −78° C.

Suitable pharmaceutically acceptable salts of the compounds of formula (XVII) include acid addition salts which may, for example, be formed by mixing a solution of the compound of formula (XVII) with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid.

The following non-limiting Examples illustrate processes according to the present invention.

EXAMPLE 1

Stereoselective Double Ring Closing Metathesis Reactions

A range of N-tosyl protected metathesis precursors were synthesised from commercially available amino acid esters as outlined in Scheme 1. Reaction of the hydrochloride salts 1a–e with tosyl chloride and triethylamine afforded the N-tosyl esters 2a–e in good yields. Cerium-mediated addition of vinylmagnesium bromide to these esters gave the tertiary alcohols 3a–e. The chirality of the tertiary alcohol 3e (R=Ph) was confirmed by chiral HPLC methods. Subsequent allylation on oxygen and nitrogen was then achieved in a single step to give the tetraenes 4a–e.

The optimum conditions for the key double RCM reaction were treatment of a 0.05M chloroform solution of the tetraene with 5–7 mol % of the Grubbs catalyst at room temperature. The easily separable spirocyclic compounds 5a–e and 6a–e were isolated in good to excellent yields. The diastereoselectivity was strongly in favour of the desired 5R,6S isomers 5a–e.

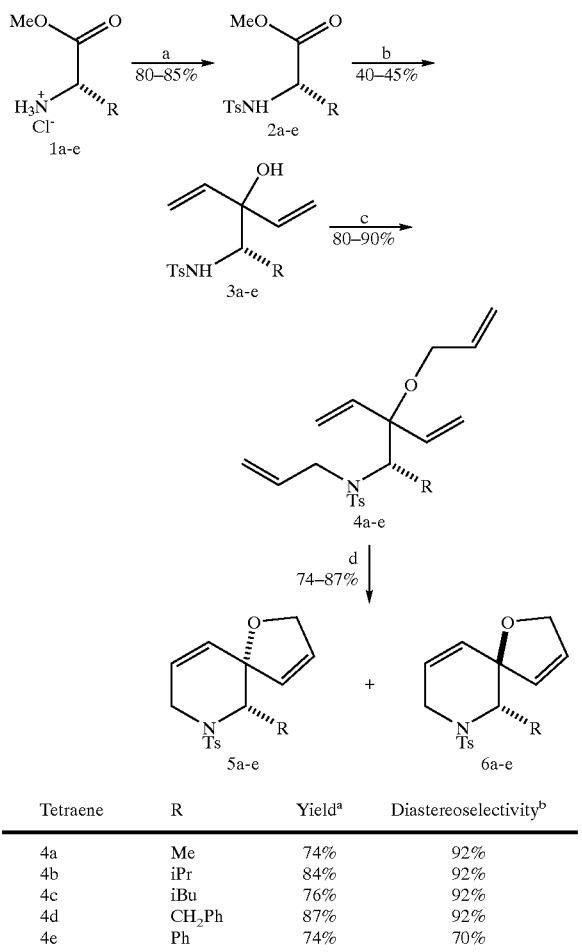

Scheme 1:
Reagents and Conditions:
(a) TsCl, Et₃N, THF, 20° C., 16 h;
(b) vinylmagnesium bromide, CeCl₃, THF, 0° C., 1 h;
(c) NaH, THF, DMPU, allyl bromide, 20° C., 16 h.
(d) RuCl₂(PCy₃)₂=CHPh, CHCl₃, 20° C., 2 h.

| Tetraene | R | Yield[a] | Diastereoselectivity[b] |
|---|---|---|---|
| 4a | Me | 74% | 92% |
| 4b | iPr | 84% | 92% |
| 4c | iBu | 76% | 92% |
| 4d | CH₂Ph | 87% | 92% |
| 4e | Ph | 74% | 70% |

[a]Isolated yield of both isomers after column chromatography
[b]Isomer ratio determined by HPLC analysis

EXAMPLE 2

Preparation of (5S)-7-aza-1-oxa-(6S)-phenyl-7-benzylspiro[4,5]deca-3,9-diene (major isomer) and (5R)-7-aza-1-oxa-(6S)-phenyl-7-benzylspiro[4,5]deca-3,9-diene (minor isomer)

Step 1—N-benzylphenylglycine

To a vigorously stirred suspension of 2-(S)-phenylglycine (10.0 g, 66.0 mmol) in water (80 mL) was added sodium hydroxide (2.65 g, 99.0 mmol) in water (10 mL) followed by benzaldehyde (6.7 mL, 66.0 mmol). Stirring was continued for 15 minutes before cooling to 0° C. whereupon sodium borohydride (0.75 g, 20 mmol) was added. The mixture was allowed to warm to room temperature and a second portion of benzaldehyde (3.0 mL, 20 mmol) was added. After 15 minutes the mixture was re-cooled and sodium borohydride (3.0 g, 7.9 mmol) added. This was then allowed to warm to room temperature and stirring continued overnight. The solids were removed by filtration and the mixture washed with ether (80 mL). The aqueous layer was then acidified to pH6 with 2N HCl causing a white solid to precipitate. This solid was filtered and dried at 40° C. under vacuum to afford the title compound as a white solid (13.0 g, 81%) which was used without further purification.

Step 2—(S)-Prop-2-enyl-2-phenyl-2-[benzylprop-2-enylamino]acetate

To a stirred suspension of the product of Step 1 (3.8 g, 16.5 mmol) in DMF (40 mL) was added diisopropylamine (6.4 mL, 36.2 mol) followed by allyl bromide (11.4 mL, 132 mmol). The mixture was then heated to 60° C. for 16 hours, before being partitioned between methyl tert-butyl ether (100 mL) and water (100 mL). The organic layer was washed with water (2×75 mL) and brine (50 mL), dried over sodium sulfate and concentrated in vacuo to give the title compound as a yellow oil which was used in the next step without purification.

$^1$H NMR (400 MHz, CDCl$_3$) δ 7.30 (m, 10H), 5.89 (m, 2H), 5.30 (dd, J=1.5, 17.2 Hz, 1H), 5.21 (m, 3H), 4.74 (s, 1H), 4.73 (ddt, J=11.0, 5.7, 1.3 Hz, 1H), 4.64 (ddt, J=11.0, 5.7, 1.3 Hz, 1H), 3.83 (d, J=14.1 Hz, 1H), 3.80 (d, J=14.1 Hz, 1H), 3.23 (d, J=6.4 Hz, 2H).

Step 3—3-{(S)-Phenyl[benzylprop-2-enylamino]methyl}penta-1,4-dien-3-ol

Anhydrous cerium chloride (9.15 g, 37.1 mmol) was dissolved in THF (50 mL) and the mixture stirred at room temperature overnight and then a solution of the product of Step 2 (2.98 g, 9.28 mmol) in THF (10 mL) was added and stirring continued for 1 hour before cooling to −10° C. Vinylmagnesium bromide (33.07 mL, 0.85M in THF, 27.8 mmol) was added and the mixture stirred for 2 hours. The mixture was partitioned between NaHCO$_3$ (40 mL) and MeOtBu (2×50 mL). The combined organics were washed with brine (50 mL), dried over sodium sulfate and concentrated in vacuo to give a yellow oil which was purified by flash column chromatography to give the title compound (1.9 g, 64%).

$^1$H NMR (400 MHz, CDCl$_3$) δ 7.28 (m, 10H), 6.13 (dd, J=10.6, 17.1 Hz, 1H), 5.79 (m, 1H), 5.77 (dd, J=10.6, 17.2 Hz, 1H), 5.47 (dd, J=1.8, 17.1 Hz, 1H), 5.18 (dd, J=1.5, 17.2 Hz, 1H), 5.10 (m, 3H), 4.93 (dd, J=1.5, 10.6 Hz, 1H), 4.21 (d, J=13.4 Hz, 1H), 3.72 (s, 1H), 3.50 (dd, J=2.0, 14.0 Hz, 1H), 2.97 (d, J=13.4 Hz, 1H), 2.64 (dd, J=8.9, 14.0 Hz, 1H).

Step 4—Benzyl (1-(S)-phenyl-2-prop-2-enyloxy-2-vinylbut-3-enyl)prop-2-enylamine

A solution of the product of Step 3 (3.23 g, 10.1 mmol) in THF (20 mL) and DMPU (20 mL) was cooled to 0° C. and sodium hydride (1.62 g, 65% dispersion, 40.5 mmol) added followed by allyl bromide (5.25 mL, 60.7 mol). The mixture was warmed to room temperature and stirred overnight. The mixture was quenched with ice cold water (5 mL) and then partitioned between water (30 mL) and MeOtBu (2×40 mL). The combined organics were washed with brine, dried over sodium sulfate and concentrated in vacuo. Purification by flash column chromatography (5% ethyl acetate in hexane) afforded the title compound (3.47 g, 95%).

$^1$H NMR (400 MHz, CDCl$_3$) δ 7.25 (m, 10H), 6.25 (dd, J=11.0, 17.7 Hz, 1H), 5.81 (m, 2H), 5.57 (dd, J=11.1, 17.6 Hz, 1H), 5.30 (dd, J=1.5, 11.0 Hz, 1H), 5.21 (dd, J=1.6, 11.1 Hz, 1H), 5.19 (dd, J=1.4, 10.6 Hz, 1H), 5.00 (m, 5H), 4.33 (d, J=14.0 Hz, 1H), 3.81 (tdd, J=1.6, 2.2, 13.3 Hz, 1H), 3.77 (tdd, J=1.6, 3.3, 13.3 Hz, 1H), 3.61 (m, 1H), 3.55 (s, 1H), 2.90 (d, J=14.0 Hz, 1H), 2.59 (dd, J=8.8, 14.3 Hz, 1H).

Step 5—(5S)-7-aza-1-oxa-(6S)-phenyl-7-benzylspiro[4,5]deca-3,9-diene (major isomer) and (5R)-7-aza-1-oxa-(6S)-phenyl-7-benzylspiro[4,5]deca-3,9-diene (minor isomer)

The tetraalkene product of Step 4 (1.07 g, 2.97 mmol) was dissolved in dichloromethane (30 mL) which was then degassed and flushed with nitrogen three times before warming to 35° C. Grubbs catalyst (RuCl$_2$(PCy$_3$)$_2$=CHPh) (220 mg, 0.267 mmol) was added, after 24 hours a further portion of catalyst (140 mg, 0.17 mmol) was added. After a further 24 hours the reaction mixture was concentrated in vacuo. The crude oil was purified by column chromatography on Florisil™ (70 g) (8% ethyl acetate in hexane) to afford the title compounds (250 mg, 28%) and (155 mg, 17%).

Major isomer (5S, 6S)

$^1$H NMR (400 MHz, C$_6$D$_6$) δ 7.45 (d, J=7.1 Hz, 2H), 7.33 (d, J=7.5 Hz, 2H), 7.19 (m, 6H), 5.82 (m, 2H), 5.45 (m, 1H), 5.22 (d, J=6.1 Hz, 1H), 4.32 (d, J=12.6 Hz, 1H), 4.03 (d, J=13.6 Hz, 1H), 3.95 (s, 1H), 3.89 (d, J=12.6 Hz, 1H), 3.19 (ddd, J=1.6, 3.7, 17.5 Hz, 1H), 2.83 (d, J=13.6 Hz, 1H), 2.66 (td, J=2.6, 17.5 Hz, 1H).

Minor isomer (5R, 6S)

$^1$H NMR (400 MHz, C$_6$D$_6$) δ 7.58 (d, J=8.4 Hz, 2H), 7.34 (d, J=8.4 Hz, 2H), 7.19 (m, 5H), 5.83 (dt, J=9.9, 2.2 Hz, 1H), 5.78 (dt, J=6.0, 2.4 Hz, 1H), 5.53 (dt, J=10.0, 3.3 Hz, 1H), 5.34 (dt, J=6.0, 1.6 Hz, 1H), 4.33 (ddd, J=12.9, 2.2, 1.8 Hz, 1H), 3.86 (ddd, J=12.9, 2.4, 1.7 Hz, 1H), 3.70 (s, 1H), 3.67 (d, J=13.5 Hz, 1H), 3.10 (d, J=13.5 Hz, 1H), 3.06 (ddd, J=17.4, 3.5, 2.2 Hz, 1H), 2.73 (dt, J=17.4, 2.7 Hz, 1H).

EXAMPLE 3

Preparation of (5R)-7-aza-7-[(4-methylphenyl)sulfonyl]-1-oxa-(6S)-phenylspiro[4.5]deca-3,9-diene (major isomer) and (5S)-7-aza-7-[(4-methylphenyl)sulfonyl]-1-oxa-(6S)-phenylspiro[4.5]deca-3,9-diene (minor isomer)

Step 1—N-Tosyl-phenylglycine, methyl ester 2e

To a solution of (S)-phenylglycine methyl ester hydrochloride salt (34.7 g, 172 mmol; 1e) in THF (400 mL) was added triethylamine (50 mL, 361 mmol) and then tosyl chloride (36.0 g, 189 mmol). The mixture was stirred at room temperature for 16 hours and then partitioned between water (300 mL) and IPAC (2×300 mL). The organic layers were washed with brine (250 mL), dried over sodium sulfate and concentrated in vacuo. The crude solid was recrystallised from methanol to give the title compound (39.2 g, 71%).

1H NMR (250 MHz, CDCl$_3$) δ 7.59 (d, J=8.3 Hz, 2H), 7.22 (m, 7H), 5.64 (d, J=7.8 Hz, 1H), 5.03 (d, J=7.8 Hz, 1H), 2.35 (s, 3H).

Step 2—(2-Hydroxy-1-(S)-phenyl-2-vinylbut-3-enyl)[(4-methylphenyl)sulfonyl]amine 3e Anhydrous cerium chloride (20.5 g, 82.5 mmol) was dissolved in THF (200 mL) and the mixture stirred at room temperature overnight and then a solution of the product of Step 2 (5.26 g, 16.5 mmol) in THF (30 mL) was added and stirring continued for 1 hour before cooling to −10° C. Vinylmagnesium bromide (68.0 mL, 0.85M in THF, 57.7 mmol) was added and the mixture stirred for 2 hours. The mixture was partitioned between citric acid (100 mL, sat. aq.) and MeOtBu (2×150 mL). The combined organics were washed with brine (100 mL), dried over sodium sulfate and concentrated in vacuo to give a yellow oil which was purified by flash column chromatography to give the title compound (3.7 g, 65%).

$^1$H NMR (400 MHz, CDCl$_3$) δ 7.35 (d, J=6.6 Hz, 2H), 7.08 (m, 3H), 6.91 (m, 4H), 5.74 (dd, J=17.0, 10.7 Hz, 1H), 5.70 (dd, J=17.1, 10.7 Hz, 1H), 5.31 (m, 2H), 5.18 (m, 2H), 5.05 (d, J=10.7 Hz, 1H), 4.26 (d, J=8.0 Hz, 1H), 2.22 (s, 3H).

Step 3—[(4-Methylphenyl)sulfonyl](1-(S)-phenyl-2-prop-2-enyloxy-2-vinylbut-3-enyl)prop-2-enylamine 4e A solution of the product of Step 3 (3.6 g, 10.5 mmol) in THF (15 mL) and DMPU (15 mL) was cooled to 0° C. and sodium hydride (2.3 g, 65% dispersion, 62.9 mmol) added followed by allyl bromide (9.0 mL, 105 mol). The mixture was warmed to room temperature and stirred overnight. The mixture was quenched with ice cold water (5 mL) and then partitioned between water (30 mL) and MeOtBu (2×40 mL). The combined organics were washed with brine, dried over sodium sulfate and concentrated in vacuo. Purification by flash column chromatography (5% ethyl acetate in hexane) afforded the title compound (3.22 g, 72%).

$^1$H NMR (400 MHz, CDCl$_3$) δ 7.45 (m, 4H), 7.18 (m, 3H), 7.04 (d, J=8.0 Hz, 1H), 6.04 (dd, J=17.4, 11.0 Hz, 1H), 5.82 (m, 1H), 5.60 (dd, J=17.4, 11.3 Hz, 1H), 5.50 (ddt, J=17.2, 10.2, 6.3 Hz, 1H), 5.31 (dd, J=4.4, 1.3 Hz, 1H), 5.28 (dd, J=1.3, 10.8 Hz, 1H), 5.21 (dq, J=17.2, 1.7 Hz, 1H), 5.10 (m, 3H), 5.02 (s, 1H), 4.90 (dq, J=17.2, 1.6 Hz, 1H), 4.79 (dq, J=10.3, 1.7 Hz, 1H), 4.21 (ddt, J=16.5, 6.3, 1.6 Hz, 1H), 3.96 (ddt, J=16.5, 6.3, 1.4 Hz, 1H), 3.81 (ddt, J=12.9, 5.2, 1.6 Hz, 1H), 3.79 (ddt, J=12.9, 5.2, 1.6 Hz, 1H), 3.61 (m, 1H).

Step 4—(5R)-7-aza-7-[(4-methylphenyl)sulfonyl]-1-oxa-(6S)-phenylspiro[4.5]deca-3,9-diene (major isomer, 5e) and (5S)-7-aza-7-[(4-methylphenyl)sulfonyl]-1-oxa-(6S)-phenylspiro[4.5]deca-3.9-diene (minor isomer, 6e)

The tetraalkene product of Step 3 (0.986 g, 2.33 mmol) was dissolved in dichloromethane (40 mL) which was then degassed and flushed with nitrogen three times. Grubbs catalyst (RuCl$_2$(PCy$_3$)$_2$=CHPh) (96 mg, 0.116 mmol) was added and the mixture stirred for 16 hours and then opened to the atmosphere and concentrated in vacuo. The crude oil was purified by column chromatography on Florisil™ (70 g) (10% ethyl acetate in hexane) to afford the title compounds (437 mg, 51%) and (195 mg, 23%).

Major isomer 5e (5R, 6S)

$^1$H NMR (400 MHz, C$_6$D$_6$) δ 7.36 (dd, J=6.6, 1.7 Hz, 2H), 7.18 (m, 2H), 7.08 (m, 3H), 7.00 (dd, J=6.6, 1.7 Hz, 2H), 5.88 (dt, J=6.0, 1.5 Hz, 1H), 5.71 (m, 2H), 5.68 (ddd, J=10.3, 3.7, 2.3 Hz, 1H), 5.12 (s, 1H), 4.58 (m, 2H), 4.07 (ddd, J=17.8, 3.7, 2.3 Hz, 1H), 3.40 (dt, J=17.8, 2.4 Hz, 1H), 2.25 (s, 3H).

Minor isomer 6e (5S, 6S)

$^1$H NMR (400 MHz, C$_6$D$_6$) δ 7.55 (dd, J=6.6, 1.7 Hz, 2H), 7.19 (m, 5H), 7.05 (dd, J=6.6, 1.7 Hz, 2H), 5.88 (ddd, J=10.1, 4.1, 2.3 Hz, 1H), 5.71 (m, 2H), 5.87 (dt, J=6.2, 1.7 Hz, 1H), 5.78 (m, 1H), 5.20 (dt, J=6.2, 2.5 Hz, 1H), 5.10 (s, 1H), 4.60 (m, 2H), 3.94 (ddd, J=18.3, 4.1, 2.3 Hz, 1H), 3.55 (dt, J=18.3, 2.3 Hz, 1H), 2.26 (s, 3H).

EXAMPLE 4

Preparation of (3R,5R,6S)-3-(2-cyclopropoxy-5-(trifluoromethoxy)phenyl)-6-phenyl-1-oxa-7-aza-spiro[4.5]decane Step 1—(3R,5R,6S)-3-(2-benzyloxy-5-(trifluoromethoxy)phenyl)-7-aza-7-[(4-methylphenyl)sulfonyl]-1-oxa-6-phenylspiro[4.5]deca-9-ene Palladium acetate (40 mg) was added to a degassed mixture of 1-benzyloxy-2-iodo-4-trifluoromethoxybenzene (172 mg), (5R)-7-aza-7-[(4-methylphenyl)sulfonyl]-1-oxa-(6S)-phenylspiro[4.5]deca-3,9-diene (53 mg, from Step 4 of Example 3, 5e), tetrabutylammonium chloride (48 mg), lithium chloride (62 mg), potassium hydrogencarbonate (43 mg) and triethylamine (61 μL) in 20:1 DMF:water (2 mL). The mixture was degassed once more, then heated at 40° C. for 4 days. The mixture was partitioned between water and ethyl acetate, and the organic extract then concentrated and chromatographed on silica gel, eluting with ethyl acetate: hexane (1:4) to give the desired product (49.5 mg, 64% yield) as an oil.

$^1$H NMR (400 MHz, CDCl$_3$) δ 7.30 (m, 7H), 7.10 (m, 6H), 6.95 (m, 3H), 6.82 (d, J=8.9 Hz, 1H), 5.84 (dd, J=10.4, 0.8 Hz, 1H), 5.71 (ddd, J=10.4, 2.4, 3.7 Hz, 1H), 5.13 (s, 1H), 5.06 (d, J=11.8 Hz, 1H), 5.03 (d, J=11.8 Hz, 1H), 4.13 (t, J=8.0 Hz, 1H), 4.04 (ddd, J=17.5, 3.7, 2.3 Hz, 1H), 3.93 (dq, J=9.9, 8.0 Hz, 1H), 3.71 (t, J=8.0 Hz, 1H), 3.39 (dt, J=17.5, 2.4 Hz, 1H), 2.64 (dd, J=12.9, 7.4 Hz, 1H), 2.22 (s, 3H), 2.03 (dd, J=10.1, 12.9 Hz, 1H).

Step 2—(3R,5R,6S)-3-(2-hydroxy-5-(trifluoromethoxy)phenyl)-7-aza-7-[(4-methylphenyl)sulfonyl]-1-oxa-6-phenylspiro[4.5]decane A solution of the Heck product of Step 1 (180 mg, 0.338 mmol) and palladium hydroxide on carbon (25.0 mg) in ethanol (5.0 mL) was flushed with nitrogen and then hydrogen and left to stir under a hydrogen atmosphere for 18 hours. The mixture was flushed with nitrogen, filtered through Celite™ and concentrated in vacuo. The crude mixture was purified by flash column chromatography (30% EtOAc in hexane) to afford the phenol as a colourless oil (140 mg, 90%).

$^1$H NMR (400 MHz, CDCl$_3$) δ 7.25 (m, 3H), 7.19 (m, 1H), 7.14 (d, J=7.6 Hz, 2H), 6.98 (d, J=7.6 Hz, 2H), 6.94 (m, 1H), 6.86 (m, 2H), 6.67 (d, J=8.6 Hz), 5.06 (s, 1H), 4.22 (dd, J=8.6, 7.4 Hz, 1H), 3.85 (m, 1H), 3.80 (m, 2H), 3.19 (td, J=12.5, 3.6 Hz, 1H), 2.86 (dd, J=13.0, 8.3 Hz), 2.27 (s, 3H), 2.18 (td, J=13.6, 4.5 Hz), 1.80 (m, 4H): $^{13}$C (100.6 MHz, CDCl$_3$) δ 153.2, 143.3, 137.3, 136.6, 129.8, 129.5, 128.4, 127.9, 127.3, 122.2 (q), 121.5, 120.8, 117.0, 84.7, 67.7, 63.6, 43.9, 41.6, 40.1, 31.5, 23.7, 21.7.

Step 3—(3R,5R,6S)-7-aza-7-[(4-methylphenyl)sulfonyl]-1-oxa-3-[2-(1-phenylthiocycloprop-1-yl)oxy-5-(trifluoromethoxy)phenyl]-6-phenylspiro[4.5]decane To a solution of the phenol of Step 2 in toluene under a nitrogen atmosphere was added silver carbonate followed by cyclopropyl iodide. After 24 hours water was added and the mixture was extracted with ethyl acetate. Following concentration and flash column chromatography the desired compound was obtained.

Step 4—(3R,5R,6S)-3-(2-cyclopropoxy-5-(trifluoromethoxy)phenyl)-6-phenyl-1-oxa-7-aza-spiro[4.5]decane A solution of the phenylthiocyclopropyl compound of Step 3 in DME was degassed and cooled to −78° C. under a nitrogen atmosphere. Freshly prepared sodium naphthalide was added until the blue colour remained in the solution. The mixture was quenched with citric acid and warmed to room temperature. This was then extracted with ether to remove the naphthalide and other organic impurities. The aqueous layer was then brought to pH12 with aqueous Na$_2$CO$_3$ and then extracted with ethyl acetate (3×10 mL). The combined organics were dried over sodium sulfate and concentrated in vacuo to give the desired amine.

$^1$H NMR (400 MHz, CDCl$_3$) δ7.38 (m, 2H), 7.25 (m, 3H), 6.91 (d, J=8.9 Hz, 1H), 6.88 (ddd, J=0.8, 2.7, 8.9 Hz, 1H), 6.76 (d, J=2.7 Hz, 1H), 3.85 (t, J=7.9 Hz, 1H), 3.49 (m, 1H), 3.43 (s, 1H), 3.12 (ddd, J=1.7, 4.5, 12.0 Hz, 1H), 2.69 (td, J=12.0, 2.7 Hz, 1H), 2.20–1.86 (m, 5H), 1.61–1.45 (m, 3H), 0.64 (dt, J=2.4, 6.1 Hz, 2H), 0.51 (m, 2H): $^{13}$C (62.5 MHz, CDCl$_3$)) δ 155.8, 143.0, 141.2, 130.8, 129.5, 128.3, 126.2, 120.5, 120.0, 113.2, 82.7, 72.2, 70.2, 51.3, 47.5, 42.5, 38.4, 38.3, 24.1, 6.6, 6.5.

What we claim is:

1. A compound of the formula (I)

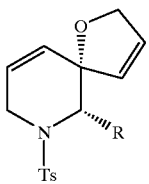

wherein Ts is a tosylate group; and
R is selected from the group consisting of:
(1) straight or branched $C_{1-4}$alkyl,
(2) benzyl,
(3) benzyl substituted with 1 or 2 substituents selected from $R^4$ and $R^5$,
(4) phenyl, and
(5) phenyl substituted with 1 or 2 substituents selected from $R^4$ and $R^5$, $R^4$ is selected from the group consisting of:
hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl and $C_{1-4}$alkyl substituted with $C_{1-4}$alkoxy,
where $R^a$ and $R^b$ each independently are selected from hydrogen, $C_{1-4}$alkyl and fluoro$C_{1-4}$alkyl;

$R^5$ is selected from the group consisting of:
hydrogen, halogen, $C_{1-6}$alkyl, $CF_3$ and $C_{1-6}$alkoxy substituted with $C_{1-4}$alkoxy;

and salts thereof.

2. The compound of claim 1 wherein R is benzyl, phenyl or phenyl substituted with $R^4$.

3. The compound of claim 2 wherein R is phenyl or 4-fluorophenyl.

* * * * *